US012653386B2

(12) United States Patent
Hansen

(10) Patent No.: US 12,653,386 B2
(45) Date of Patent: Jun. 16, 2026

(54) ENDOSCOPE COMPRISING A BENDING SECTION HAVING A VARYING LENGTH OF HINGES

(71) Applicant: AMBU A/S, Ballerup (DK)

(72) Inventor: Frederik Clausager Vemb Hansen, Copenhagen NV (DK)

(73) Assignee: AMBU A/S, Ballerup (DK)

( * ) Notice: Subject to any disclaimer, the term of this patent is extended or adjusted under 35 U.S.C. 154(b) by 265 days.

(21) Appl. No.: 18/289,311

(22) PCT Filed: May 18, 2022

(86) PCT No.: PCT/EP2022/063419
§ 371 (c)(1),
(2) Date: Nov. 2, 2023

(87) PCT Pub. No.: WO2022/243363
PCT Pub. Date: Nov. 24, 2022

(65) Prior Publication Data
US 2024/0225428 A1 Jul. 11, 2024

(30) Foreign Application Priority Data

May 20, 2021 (DE) .......................... 102021113183.9

(51) Int. Cl.
*A61B 1/008* (2006.01)
*A61B 1/00* (2006.01)
*A61B 1/005* (2006.01)

(52) U.S. Cl.
CPC ............ *A61B 1/008* (2013.01); *A61B 1/0055* (2013.01); *A61B 1/00045* (2013.01); *A61B 1/0052* (2013.01)

(58) Field of Classification Search
CPC ...... A61B 1/0052; A61B 1/0055; A61B 1/008
See application file for complete search history.

(56) References Cited

U.S. PATENT DOCUMENTS 3,060,972 A * 10/1962 Sheldon ............... A61B 1/0055
138/120
3,162,214 A 12/1964 Bazinet, Jr.
(Continued)

FOREIGN PATENT DOCUMENTS

EP 2010039 B1 9/2014
JP H03170125 A 7/1991
(Continued)

OTHER PUBLICATIONS

ISRWO in International Application No. PCT/EP2022/063419, mailed Aug. 30, 2022, 13 pages.
(Continued)

*Primary Examiner* — Aaron B Fairchild
(74) *Attorney, Agent, or Firm* — Faegre Drinker Biddle & Reath LLP

(57) ABSTRACT

An endoscope including a handle; and an insertion cord including a bending section made from one or two pieces of polymer material; the bending section including: bending segments and bendable hinges keeping together the bending segments, the hinges each having a specific hinge length; the bending section having a portion in which the hinge length predominantly increases from a proximal end segment of said portion to a distal end segment of said portion; and the portion including at least one trigger point formed by an abrupt increase in the hinge length.

31 Claims, 5 Drawing Sheets

(56)                References Cited

U.S. PATENT DOCUMENTS

| | | | |
|---|---|---|---|
| 4,911,148 | A | 3/1990 | Sosnowski et al. |
| 5,174,277 | A * | 12/1992 | Matsumaru .......... A61B 1/0055 |
| | | | 600/142 |
| 5,284,128 | A * | 2/1994 | Hart ................. A61B 17/00234 |
| | | | 600/209 |
| 5,297,443 | A | 3/1994 | Wentz |
| 5,325,845 | A | 7/1994 | Adair |
| 5,928,136 | A | 7/1999 | Barry |
| 6,428,489 | B1 * | 8/2002 | Jacobsen ............... A61M 25/09 |
| | | | 600/585 |
| 8,007,434 | B2 | 8/2011 | Olson |
| 9,172,227 | B2 | 10/2015 | Kitagawa |
| 9,968,241 | B2 | 5/2018 | Iuel |
| 9,987,460 | B2 | 6/2018 | Brustad et al. |
| 10,165,931 | B2 | 1/2019 | Petersen et al. |
| 10,321,804 | B2 | 6/2019 | Jacobsen et al. |
| 10,369,328 | B2 | 8/2019 | Tsai et al. |
| 11,357,392 | B2 | 6/2022 | Matthison-Hansen et al. |
| 11,471,031 | B2 | 10/2022 | Jensen |
| 2004/0044270 | A1 * | 3/2004 | Barry ................... A61B 1/0056 |
| | | | 600/142 |
| 2007/0208224 | A1 * | 9/2007 | Olson ................. A61M 25/007 |
| | | | 600/141 |
| 2009/0137875 | A1 * | 5/2009 | Kitagawa ............. A61B 1/0055 |
| | | | 600/146 |

| | | | |
|---|---|---|---|
| 2013/0261396 | A1 | 10/2013 | Boulais et al. |
| 2014/0024898 | A1 | 1/2014 | Konstorum |
| 2016/0243697 | A1 * | 8/2016 | Sato ...................... A61B 34/70 |
| 2017/0065153 | A1 * | 3/2017 | Fujitani .............. A61B 1/00112 |
| 2020/0037851 | A1 | 2/2020 | Okita |
| 2020/0037852 | A1 | 2/2020 | Takahashi et al. |
| 2020/0100648 | A1 | 4/2020 | Jensen |
| 2020/0113412 | A1 | 4/2020 | Jensen |
| 2020/0113415 | A1 | 4/2020 | Kristensen |
| 2020/0196835 | A1 | 6/2020 | Qvist et al. |
| 2020/0257105 | A1 | 8/2020 | Okita |
| 2021/0045626 | A1 * | 2/2021 | Hsu ........................ A61B 1/307 |
| 2021/0393113 | A1 | 12/2021 | Matthison-Hansen |
| 2022/0117462 | A1 * | 4/2022 | Hansen ................ A61B 1/0011 |
| 2023/0128263 | A1 * | 4/2023 | Major .............. A61M 25/0147 |
| | | | 606/130 |

FOREIGN PATENT DOCUMENTS

| | | |
|---|---|---|
| WO | 2019018736 A2 | 1/2019 |
| WO | 2020106705 A1 | 5/2020 |

OTHER PUBLICATIONS

Search report, with translation, in German Application No. 10 2021 113 183.9, mailed Jan. 24, 2022, 21 pages.

* cited by examiner

13

ENDOSCOPE COMPRISING A BENDING SECTION HAVING A VARYING LENGTH OF HINGES

CROSS REFERENCE TO RELATED APPLICATIONS

This application is a National Stage entry under 35 U.S.C. § 371 of International Application No. PCT/EP2022/063419, filed May 18, 2022, which claims the benefit of and priority from German Patent Application No. 10 2021 113 183.9, filed May 20, 2021; the disclosures of the aforementioned applications are incorporated by reference herein in their entirety.

The present disclosure relates to a (single-use) endoscope comprising: an endoscope handle; and an insertion cord configured to be inserted into a patient's body cavity and comprising a bendable bending section made from one or two pieces of polymer material, the bending section comprising: a plurality of bending segments; and a plurality of bendable hinges keeping together and formed integrally with the plurality of bending segments.

RELATED ART

Endoscopes and similar specialized instruments such as bronchoscopes, arthroscopes, colonoscopes, laparoscopes, gastroscopes, duodenoscopes and ureteroscopes are well known from the state of the art and are used for visual examination and diagnosis of hollow organs and body cavities, as well as to assist in surgery, e.g. for a targeted tissue sampling. Basically, a distal tip unit of an endoscope, which is connected to a proximal endoscope handle via a bending section and an insertion tube, can be inserted into a hollow organ or body cavity to be investigated with the endoscope. Both reusable and disposable (i.e. single-use) endoscopes are known from the state of the art.

Known endoscopes usually contain steering/control wires that are pulled and released to bend the (flexible) bending section of the endoscope, in order to tilt the distal tip unit. In order to achieve a bending of the bending section, a rotating force being applied to e.g. a handle wheel or a lever provided at the proximal endoscope handle by a user may basically be transmitted into a pulling force acting on the steering wires in an axial direction of the steering wires.

Single-use endoscopes are already known which have a bending section molded in one single piece or two single pieces of a polymer material. The bending section of such a single-use endoscope comprises a number of rigid bending segments kept together by bendable hinges/hinge members. Generally, the hinge dimensions and the hinge layout determine a bending profile (in particular a bending radius and a bending angle) of the bending section. In this context it is e.g. known from the prior art to provide a uniform hinge design, i.e. to provide uniform hinges having constant width and length from a proximal end of the bending section to a distal end of the bending section.

Basically, it is desirable to provide a circular bending profile with a constant bending radius. I.e. it is desirable that the bending profile of the bending section rather follows or is closer to a perfect circle than to an ear-shape. This aim has turned out to be difficult to achieve with some single-use endoscopes (e.g. with single-use endoscopes having a bending section, which is both long and thin, i.e. a bending section having a high ratio of length of the bending section to diameter of the bending section), in particular in case a uniform hinge design is provided. An example of an endoscope having a high ratio of length of the bending section to diameter of the bending section is an ureteroscope. It has in particular turned out that with an increasing length of a bending section having a uniform hinge design, the bending profile can be described such that the bending radius continuously increases from a proximal end of the bending section to a distal end of the bending section, so that the bending profile rather follows an ear-shape.

From U.S. Pat. No. 10,321,804 B2 a single-use endoscope having a bending section with a non-uniform hinge design is already known. In particular, it is disclosed that a thickness/width of the flexible hinges/hinge members continuously increases from a distal end of the bending section to a proximal end of the bending section. U.S. Pat. No. 10,321,804 B2 thus discloses a single-use endoscope having a bending section with a varying stiffness, in particular with a lower stiffness at the distal end of the bending section and a higher stiffness at the proximal end of the bending section. However, also with the design known from said document, no circular bending profile can be achieved when the bending section is both long and thin. Moreover, a varying/increasing hinge width/thickness may increase strain/stress in the widest hinges and hence the risk of permanent deformation. Further, it has turned out that kinking occurs in the hinges and that the bending profile is very sensitive to even small changes in the width.

U.S. Pat. No. 3,060,972 discloses a flexible reusable endoscope having a bending section. In the bending section circular bending elements and separate spacer annular elements like washers or sleeves are provided. The spacer annular elements are provided between the circular bending elements. The bending section has sections with different bending radii. In particular, different lengths of the spacer annular elements cause the variation of the bending radii. If a large bending radius is desired, annular elements having shorter lengths shall be used, and if a small bending radius is desired, annular elements having longer lengths shall be used. According to the disclosure of U.S. Pat. No. 3,060,972 it is desirable that a distal portion of the bending section is flexed first, while a proximal portion of the bending section remains straight. Providing a bending section consisting of circular bending elements and separate spacer annular elements like washers or sleeves however is not suitable for a single-use endoscope due to high manufacturing costs.

U.S. Pat. No. 5,297,443 discloses a flexible positioning arm suitable for a reusable endoscope. The flexible positioning arm includes a plurality of resiliently coupled rigid segments, which can be pulled in a curve using control lines. According to the disclosure of said document, a relatively stiffer proximal section for general positioning and a relatively flexible distal section for fine positioning may be provided. Further, only the distal end may be bent by varying the dimensions and the flexibility of joints provided between the rigid segments. The joints are formed as springs or other resilient couplings between the segments, and a length of the spring/of the other resilient coupling between the segments may be varied. In particular, shorter (stiffer) connections can be provided near the proximal end and longer (more flexible) connections can be provided approaching the distal end of the flexible positioning arm, where greater flexibility is desired. The flexible positioning arm disclosed in U.S. Pat. No. 5,297,443 is however also not suitable for a single-use endoscope due to high manufacturing costs.

BRIEF DESCRIPTION OF THE DISCLOSURE

The tasks and objectives of the present disclosure are to eliminate or at least to reduce the disadvantages of the prior art. In particular, a single-use endoscope shall be provided, in which a bending section achieves or at least approximates a circular bending shape/profile when the bending section is fully bent through a more even distribution of bending forces along the length of the bending section. Stress and strain in hinges between bending segments, especially in proximal hinges, shall be minimized as much as possible when the bending section is bent.

The tasks and objectives of the present disclosure are solved by an endoscope in accordance with claim 1 and by a system in accordance with claim 30. Advantageous embodiments are claimed in the dependent claims and/or are explained below.

In the present disclosure, "proximal" basically means "in a direction away from a patient towards a user", and "distal" basically means "in a direction towards the patient away from the user".

The present disclosure relates to a (single-use) endoscope comprising: an endoscope handle; and an insertion cord configured to be inserted into a patient's body cavity and comprising a bendable bending section made from one or two pieces of polymer material; the bending section comprising: a plurality of bending segments; and a plurality of bendable hinges keeping together and formed integrally with the plurality of bending segments, the plurality of hinges each having a specific hinge length; the bending section having a portion/section in which the hinge length predominantly/overall increases from a proximal end segment of said portion/section to a distal end segment of said portion/section; and said portion/section comprising at least one trigger point formed by an abrupt increase in the hinge length.

By providing bendable hinges having hinge lengths, which overall/predominantly increase in a proximal-distal direction in said portion of the bending section, a stiffness of the individual hinges predominantly/overall decreases in the proximal-distal direction. Said differently, proximal hinges of the plurality of bendable hinges may be shorter (in their hinge lengths) and thus may have a higher stiffness than distal hinges of the plurality of hinges.

According to the present disclosure, a stiffness of the hinges provided in said portion of the bending section is thus varied in the proximal-distal direction by suitably setting/changing/selecting the hinge length of the hinges. Advantageously a bending curvature of the bending section may therefore be controlled by selecting the ideal stiffness of hinges (i.e. the ideal hinge length) in dependence of/based on the position along a proximal-distal axis.

According to the present disclosure, it has in particular turned out that by providing hinges having different hinge lengths, in particular overall/predominant increasing hinge lengths in the proximal-distal direction (i.e. proximal hinges being shorter than distal hinges), the bending curvature can be set so as to be close to the curvature of a circle, in particular compared to uniform hinges having uniform hinge lengths, which rather provide an ear-shaped bending curvature, in particular in case the bending section is long and has a small diameter.

It is to be understood, that the mentioned portion of the bending section may constitute the entire bending section or may constitute only a part/portion/section of the bending section. Said differently, it may e.g. be provided that an individual bending segment/an individual hinge or a plurality of individual bending segments/hinges e.g. at the proximal end of the bending section or at the distal end of the bending section do not form part of said portion of the bending section. In case said portion constitutes/forms/is the entire bending section, then one could say that the hinge length preferably overall/predominantly increases from the proximal end segment of the bending section to the distal end segment of the bending section.

According to the present disclosure, the hinge length overall/predominantly increases from the proximal end segment of said portion of the bending section towards the distal end segment of said portion of the bending section. I.e. it is not essential or required that the hinge length gradually/continuously increases in the proximal-distal direction. Said differently there may e.g. be/exist adjacent hinges in said portion of the bending section in which the hinge length remains constant or even decreases, as long as the hinge length between the proximal end segment of said portion and the adjacent (distal) segment is smaller than the hinge length between the distal end segment of said portion and the adjacent (proximal) segment.

It can also be said that the present disclosure relates to an endoscope comprising a bending section having a varying length of hinges, in particular overall/predominant increasing length of hinges in the proximal-distal direction.

According to the present disclosure, said portion of the bending section comprises at least one abrupt/sudden change in hinge length. Said abrupt change in hinge length is designated as a trigger point. The trigger point basically serves to divide the mentioned portion of the bending section at least into two sub-sections. It is to be added that there may also be provided more sub-sections, such as three, four, five or six.

It has in particular turned out that by the provision of such a trigger point/trigger points not only the curvature of the fully bent bending section can be influenced but also the way the bending section bends form a starting point, at which the bending section is straight, until it is fully bent. Advantageously, the bending section of the present disclosure does not start the bending primarily at the proximal end of the bending section, like it is the case for uniform (equal-length) hinges. Instead, the bending section in accordance with the present disclosure preferably starts the bending also at the distal end of the bending section, resulting in a better bending shape and reducing the stress in the proximal hinges. The trigger point preferably enables that the bending starts also in the distal end of the bending section.

It can thus be said that the bending section preferably is configured so as to start bending at/around the trigger point.

According to a preferred embodiment, the trigger point is configured to divide said portion of the bending section into a series of at least two levers.

It has turned out that the bending section according to the present disclosure can be considered as a system of levers. In case the hinge length is the same or changes gradually over the length of the bending section (i.e. without any abrupt increase in hinge length), which is not preferred according to the present disclosure, the bending section functions as one long lever, i.e. a high amount of the force applied at a distal tip will travel/go to the root and get absorbed into deformation/bending of the most proximal hinges. On the other hand, in case the hinge length changes abruptly over a trigger point, which is preferred according to the present disclosure, the bending section functions as a series of smaller levers and a certain amount of the force applied at the distal tip will only travel to and get absorbed into deformation/bending of the trigger point/hinge, so that only a smaller amount of the force will travel to and get absorbed into deformation/bending of the most proximal hinges.

Said differently, the trigger point preferably effectively breaks the "long lever" constituting the bending section into a series of "smaller/shorter levers", so that forces applied at the distal tip will to a higher degree only travel and exert deformation to the last/distal-most trigger point. By incorporating at least one trigger point, the bending forces can be distributed more evenly throughout the bending section and a more circular bending shape is created. Moreover, it has shown that the addition of at least one trigger point reduces strain/stress in the proximal hinges of the bending section.

To sum up, according to the present disclosure, it has appeared that a gradual/continuous increase in hinge length in the proximal-distal direction is not necessarily preferred. In particular, experiments and simulations have shown that dividing the bending section into minor (sub)sections and introducing an abrupt change in hinge length between these (sub)sections is preferable compared to a gradual/continuous increase in hinge length in the proximal-distal direction.

According to a preferred embodiment, the increase in the hinge length at the trigger point is greater than between any other adjacent bendable hinges provided in said portion of the bending section.

There may in particular be a (sub)portion/(sub)section of the bending section in which the hinge length gradually increases, resulting in a gradual small increase in hinge lengths between adjacent bendable hinges. The increase in hinge length at the trigger point should at least be (much) greater than the maximum increase between adjacent hinges in such a (sub)portion/(sub)section of the bending section, in which the hinge length gradually increases.

A preferred embodiment is characterized in that the increase in hinge length is at least the double, preferably at least the triple, of an average increase in hinge length from the proximal end segment of said portion of the bending section to the distal end segment of said portion of the bending section.

The average increase in hinge length a may in this context be defined as the length of the distal most hinge $hl_d$ of said portion minus the length of the proximal most hinge $hl_p$ of said portion divided through the number of bending segments n in said portion.

$$a = (hl_d - hl_p)/n \qquad \text{Equation (1)}$$

Especially preferred, the hinge length increases from the proximal end segment of the bending section to the distal end segment of the bending section, and at least one trigger point is provided where an increase in hinge length is at least the double, preferably at least the triple, of an average increase in hinge length from the proximal end segment of the bending section to the distal end segment of the bending section.

Preferably, the trigger point is formed as an abrupt increase in hinge length over one bending segment or a few bending segments. One could also say that the trigger point is preferably formed as an abrupt increase in hinge length, considering the increase between two hinges or more hinges, e.g. three or four. According to a preferred embodiment of the present disclosure, the abrupt increase in hinge length is present between only two adjacent hinges (the increase over one bending segment which is located between these two adjacent hinges). However, the present disclosure is not limited to said preferred embodiment, and it is also conceivable that the abrupt increase in hinge length forming the trigger point is present between three or more adjacent hinges (the increase over two or more bending segments which are located between the two outer hinges of the three or more adjacent hinges).

According to a preferred embodiment, at least two trigger points are provided in said portion of the bending section. Said differently, preferably at least two abrupt changes in hinge length are provided in said portion of the bending section. This also means that preferably said portion of the bending section comprises a series of at least three levers.

Advantageously, said preferred embodiment achieves that an even more circular bending shape is reached when the bending section is fully bent, that forces are even better distributed throughout the bending section, that the bending at the distal end of the bending section starts even earlier, and that even less stress/strain is introduced into the proximal hinges of the bending section.

Preferably, it may apply that the increase in hinge length at both trigger points is greater than between any other adjacent bendable hinges provided in said portion. Further preferred, for each of the at least two trigger points it may apply that the increase in hinge length is at least the double, preferably at least the triple, of the average increase in hinge length from the proximal end segment of said portion to the distal end segment of said portion.

It is to be added that there may also be provided more than two trigger points, e.g. three, four, five, etc. trigger points.

Preferably, it applies for any of three adjacent bending segments of said portion of the bending section including a first proximal segment, a second middle segment and a third distal segment that a hinge length between the second middle segment and the third distal segment is greater than or equal to a hinge length between the first proximal segment and the second middle segment. According to said preferred embodiment, it is thus provided that there is no decrease in hinge length in said portion of the bending section, i.e. that the hinge lengths increase or remain constant in the proximal-distal direction. There is thus preferably no increase in stiffness in the proximal-distal direction.

Preferably, it applies for the entire bending section that for any of three adjacent bending segments including a first proximal segment, a second middle segment and a third distal segment the hinge length between the second middle segment and the third distal segment is greater than or equal to a hinge length between the first proximal segment and the second middle segment.

The bending section may comprise three sections, namely a first proximal section, a second middle section and a third distal section, and the trigger point may be formed as an abrupt change in hinge length between the first proximal section and the second middle section, and/or the trigger point may be formed as an abrupt change in hinge length between the second middle section and the third distal section. Especially preferred, a gradual increase in hinge length is provided in the first proximal section, a constant hinge length is provided in the second middle section, and a constant hinge length is provided in the third distal section.

There may e.g. be provided an especially preferred embodiment, according to which the bending section comprises three sections, namely the first proximal section, the second middle section and the third distal section, wherein a gradual increase in hinge length is provided in the first proximal section, a constant hinge length is provided in the second middle section, and a constant hinge length is provided in the third distal section, and wherein a first trigger point is formed as an abrupt change in hinge length between the first proximal section and the second middle section and a second trigger point is formed as an abrupt change in hinge length between the second middle section and the third distal section. It has in particular appeared according to the present disclosure that said especially preferred embodiment provides a desired and much improved bending performance.

Alternatively, it may e.g. also be provided that the bending section comprises three sections, namely the first proximal section, the second middle section and the third distal section, wherein a gradual increase in hinge length is provided in the first proximal section, a constant hinge length is provided in the second middle section, and a constant hinge length is provided in the third distal section, and wherein only one trigger point is formed as an abrupt change in hinge length between the second middle section and the third distal section.

The hinge length may vary in an interval of 0.3 mm to 2 mm, preferably in an interval of 0.3 mm to 1 mm, more preferably in an interval of 0.3 mm to 0.6 mm. In particular, it has appeared according to the present disclosure that for hinges having a hinge length shorter than 0.3 mm, it will be difficult to make a durable molding tool for the bending section. Further, for hinges longer than 0.6 mm it will be difficult to provide a bending section, which is both long and thin, having a sufficient torsional stiffness. For some purposes however, it may be possible to achieve a sufficient torsional stiffness at a hinge length up to 1 mm or even 2 mm.

Preferably, a diameter of the bending section is less than 3 mm. Further preferred, a length of the bending section is at least 40 mm.

The hinge length may increase by at least 0.03 mm and maximum 0.15 mm or maximum 0.25 mm at the trigger point. Therefore, especially preferred, an increase in hinge length of at least 0.03 mm may be understood as an abrupt increase in hinge length according to the present disclosure.

The plurality of hinges may have a specific hinge width, wherein the hinge width is constant over said portion of the bending section. In particular, it has turned out that a varying/increasing hinge width/thickness may increase strain/stress in the widest hinges, in particular during repeated bending of the bending section, and hence the risk of permanent deformation/of failure of the bending section. Further, it has turned out that kinking may occur in the hinges in case the hinge width is varied and that the bending profile is very sensitive to even small changes in the width. It is thus preferable according to the present disclosure that the hinge width is constant.

Further, a length of the bending segments may predominantly/overall decrease from the proximal end segment of said portion of the bending section to the distal end segment of said portion of the bending section. It is thus preferred to make the bending segments in the bending section shorter as/when the hinges are made longer (i.e. in the proximal-distal direction). This further increases the flexibility and reduces the stiffness in the distal end of the bending section. Therefore, bending may start easier also in the distal end of the bending section, and it is easier to obtain a circular bending profile.

The bending section may be configured so as to bend at least approximately in a circular shape.

Further, the bending section may be configured so as to start bending both at a proximal end portion and a distal end portion of the bending section.

The endoscope of the present disclosure is preferable a single-use endoscope. The (single-use) endoscope may be a small-diameter endoscope, in particular an ureteroscope.

According to the present disclosure, the bending section is made from/consists of one or two pieces of polymer material and the bendable hinges are integrally (monobloc, one piece, one material) formed with the bending segments. Preferably, the bending section is made from one piece of polymer material. The polymer material is preferable a thermoplastic polymer material, in particular POM (polyoxymethylene).

The endoscope may comprise a steering wire/steering wires for controlling a bending movement of the bending section of the insertion cord.

The endoscope may comprise an operating unit, e.g. a lever or a handle wheel, provided for operating the steering wire(s) and for bending the bending section of the insertion cord in a bending plane. The endoscope may also comprise two operating units, e.g. two levers/handle wheels provided for operating the steering wire(s) and for bending the bending section of the insertion cord in a first bending plane and a second bending plane.

The insertion cord may comprise an insertion tube and a distal tip unit, in addition to the bending section.

The present disclosure further relates to a system comprising an endoscope as described above and a monitor.

BRIEF DESCRIPTION OF THE FIGURES

The disclosure is explained in more detail below using preferred embodiments and referring to the accompanying figures.

The figures are schematic in nature and serve only to understand the disclosure. The features of the different embodiments can be interchanged among each other.

DETAILED DESCRIPTION OF PREFERRED EMBODIMENTS

Figures 1, 2, 3:
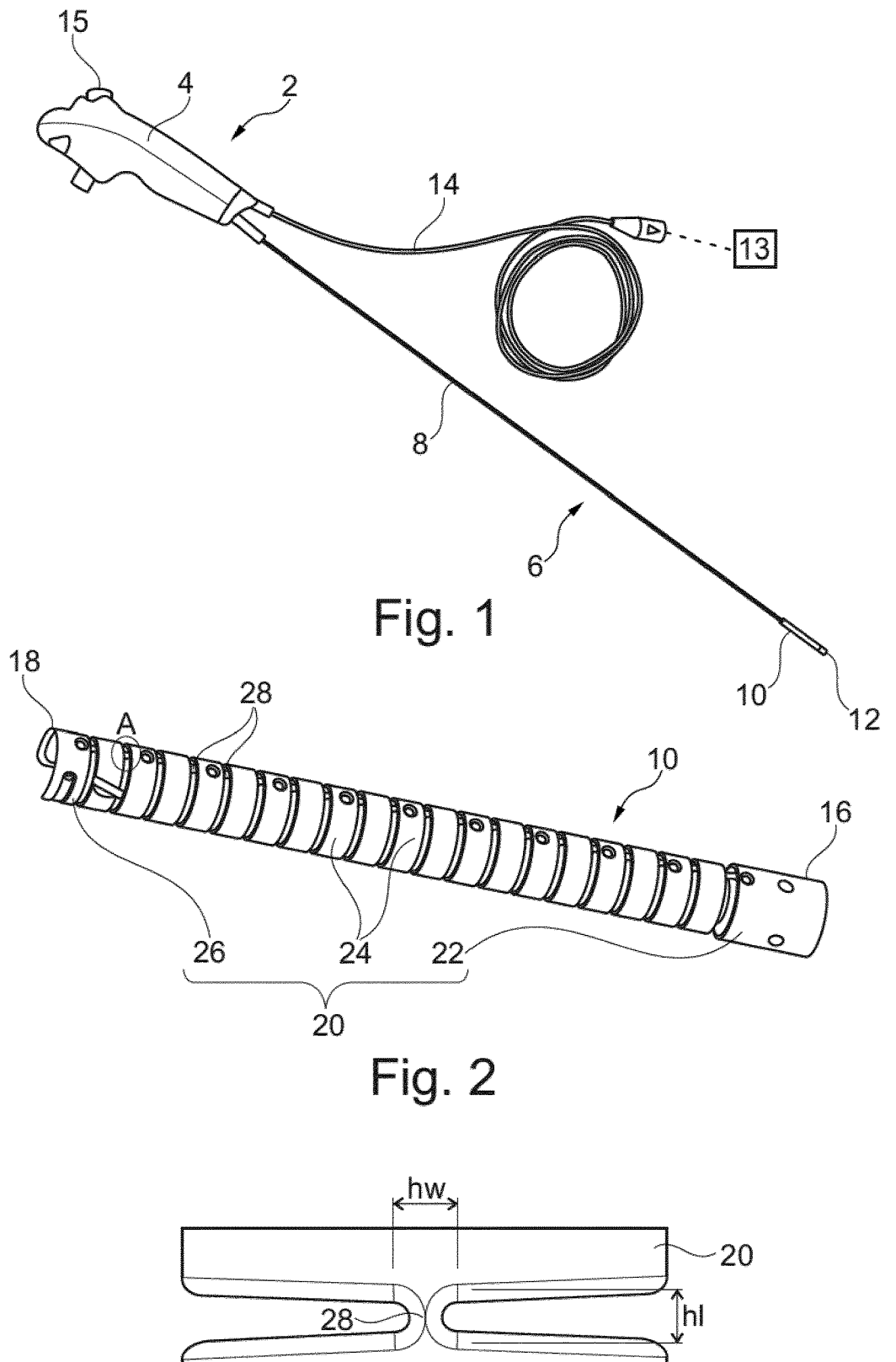
FIG. 1 is a perspective view showing an endoscope according to the present disclosure.
FIG. 2 is a perspective view showing a bending section of the endoscope.
FIG. 3 is a detail view of detail A of FIG. 2, showing a bendable hinge of the bending section.

In FIG. 1, an endoscope 2 is shown. The endoscope 2 is preferably a single-use endoscope. The endoscope 2 is preferably, but not necessarily, a small-diameter endoscope such as an ureteroscope. The endoscope 2 comprises a proximal endoscope handle 4 designed to be held by a user/physician and being configured to accommodate operating parts of the endoscope 2. Further, the endoscope 2 comprises an insertion cord 6, which is configured to be inserted into a patient's body cavity. The insertion cord 6 comprises an insertion tube 8, a bending section 10 and a distal tip unit 12, extending in this order from the proximal endoscope handle 4. A small-diameter endoscope 2 may have a diameter at the bending section 10 and the distal tip unit 12 less than or equal to 3.2 mm, preferably less than or equal to 3.0 mm, and may include a working channel tube providing a working channel extending from the endoscope handle 4 to the distal tip unit 12.

Figure 12:
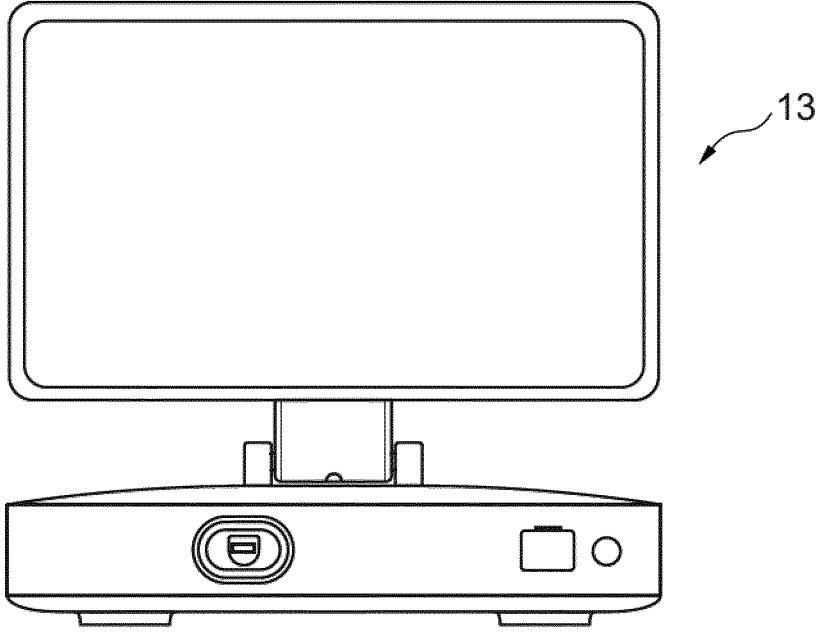
FIG. 12 is a front view of a monitor connectable to the endoscope according to the present disclosure.

At the distal tip unit 12, image capturing means such as a miniature video camera and illuminating means such as light-emitting diodes or optical fibers connected to a proximal source of light are arranged/installed, such that the patient's body cavity can be illuminated and inspected. An image captured by the image capturing means can be shown on a monitor 13, which is illustrated in FIG. 12. The monitor 13 is provided separately from and connected/connectable with the endoscope 2 via a cable 14 or wirelessly.

The endoscope handle 4 comprises an operating unit 15, which is preferably formed as a lever, for steering the bending section 10 of the insertion cord 6. In particular, a rotation/turning force can be applied to the operating unit 15 by the user. The distal tip unit 12 may be tilted/moved by bending the bending section 10. In particular, the operating unit 15 can be operated by the user to tilt the distal tip unit 12 in a bending plane (e.g. up-down). The bending section 10 may be largely covered by a flexible cover for preventing contamination.

The endoscope 2 may comprise steering wires (not shown) for controlling the bending movement of the bending section 10. The steering wires may be connected to the operating unit 15. The steering wires may extend through the insertion tube 8 and the bending section 10. By turning the operating unit 15, steering wires/steering wire portions can be pulled and released and the distal tip unit 12 can tilt according to a direction in which the operating unit 15 is rotated. In other words, by operating the operating unit 15 the user is able to tilt the distal tip unit 12 in the bending plane by bending the bending section 10 correspondingly.

It is to be understood that although FIG. 1 shows a one-plane bending endoscope, the present disclosure is not limited to the endoscope 2 being a one-plane bending endoscope. I.e. the endoscope 2 may also be a two-plane bending endoscope configured for bending in a first bending plane and a second bending plane, wherein the second bending plane is preferably perpendicular to the first bending plane.

In one variation, the monitor 13 includes a housing, a receptacle to receive a connector of the cable 14, and a handle that also functions as a table stand when the monitor 13 is positioned on a table or other support structure. The housing encloses a display screen and circuitry operable to configure the live video captured by the image sensor of the camera of the endoscope 2 to the requirements of the display screen. The circuitry also generates a graphical user interface configured to enable the operator to control the image or video capture and presentation functions, as is known in the art.

In one variation, the monitor 13 includes a housing and a receptacle to receive a connector of the cable 14, but it does not include a display screen. The housing, in this variation, includes a display support interface, which supports a display device having a display screen via a support arm. The display device can be separated or removed from the monitor 13.

Both variations of the monitor 13 may perform the same video processing functions. The processed video can be presented with a remote or separate display device communicatively connected, via a wired or wireless connection, with the monitor 13. This enables placement of the monitor 13 in a location distinct from the location of the separate display device. This also enables use of a display device available in the operating room for other purposes.

A position interface functions to control the position of the insertion cord 6. The handle 4 is an example of a position interface and, unless stated otherwise, the terms are used interchangeably. The handle 4 also functions to provide manual control actuators, e.g. operating unit 15, knobs, levers, buttons, and the like, to steer the distal tip unit 12 and control instruments guided through the insertion cord 6. Alternatively, a different position interface can be provided that is connected to the insertion cord 6 and is detachably connected to a robotic arm. The insertion cord 6 thus extends from the robotic arm, and the endoscope 2 is thus detachable from the robotic arm. The distal tip unit 12 is the same regardless of the position interface used. The robotic arm responds to signals, such as voice commands from the operator, to rotate, translate, and otherwise position the proximal end of the insertion cord 6, as an operator would do manually. The position interface can include control actuators, including manual control actuators. Alternatively or additionally, control actuators can be provided in or on the robotic arm or by the robotic system including the robotic arm, thereby potentially reducing the cost of the endoscope 2. Example control actuators include single axis actuators, including linear motion actuators. A linear motion actuator may comprise a threaded rod coupled to a threaded nut portion, in which a motor rotates the rod to translate the nut portion.

FIG. 2 shows the bending section 10 of the endoscope 2. The bending section 10 has a proximal end 16 and a distal end 18 and comprises a plurality of bending segments 20 including a proximal end segment 22, a plurality of intermediate segments 24 and a distal end segment 26. A plurality of bendable hinges 28 keeps together the plurality of bending segments 20 and is formed integrally with the plurality of bending segments 20. Two adjacent bending segments 20 are connected by a bendable hinge 28.

The bending section 10 is an integral part being formed as a single/one piece from (thermoplastic) polymer material, in particular polyoxymethylene (POM), and being preferably manufactured in an injection-molding process. It is to be understood that the bending section 10 may also be formed by assembling two pieces, each piece made of polymer material (and thus not one piece). Therefore, the bending section 10 of the present disclosure, which consists of the plurality of bending segments 20 and the plurality of hinges 28 connecting/keeping together the plurality of bending segments 20, is either formed in one piece or in two pieces, from polymer material.

The plurality of hinges 28 each have a specific hinge length hl, as shown in FIG. 3, which is a detail view of detail A shown in FIG. 2. The hinge length hl may be also defined as the distance between two adjacent bending segments 20. Moreover, the plurality of hinges 28 each have a specific hinge width hw, as also shown in FIG. 3.

According to the present disclosure, the hinge length hl overall/predominantly increases from the proximal end 16 of the bending section 10 to the distal end 18 of the bending section 10. When the length of the hinges 28 (i.e. the hinge length hl) increases in the proximal-distal-direction, the stiffness of the hinges 28 decreases in the proximal-distaldirection. Proximal hinges 28 are thus preferably shorter and therefore stiffer, whereas distal hinges 28 are longer and less stiff. Therefore, the stiffness of the bending section 10 preferably decreases from the proximal end 16 to the distal end 18. The hinge width hw is preferably constant along the entire bending section 10. The hinge thickness is preferably constant, however may alternatively be varied.

The reason for the overall/predominant increasing hinge length hl is as follows: According to the present disclosure it has been found that a bending profile (bending radius and bending angle) can be suitably adjusted/set such that a rather circular bending profile, an early activation of the distal tip/the distal end 18 of the bending section 10 and decreased stress/strain in proximal hinges 28 can be reached by providing a variable hinge design. In order to illustrate this, FIG. 4 shows a bending profile of a bending section 10, which is long and thin, having a uniform hinge design (i.e. hinges 28 have constant hinge length hl and constant hinge width hw from the proximal end 16 of the bending section 10 to the distal end 18 of the bending section 10), and FIG. 5 shows a bending profile of a bending section 10, which is long and thin, having a non-uniform, i.e. a variable hinge design.

Figure 4:
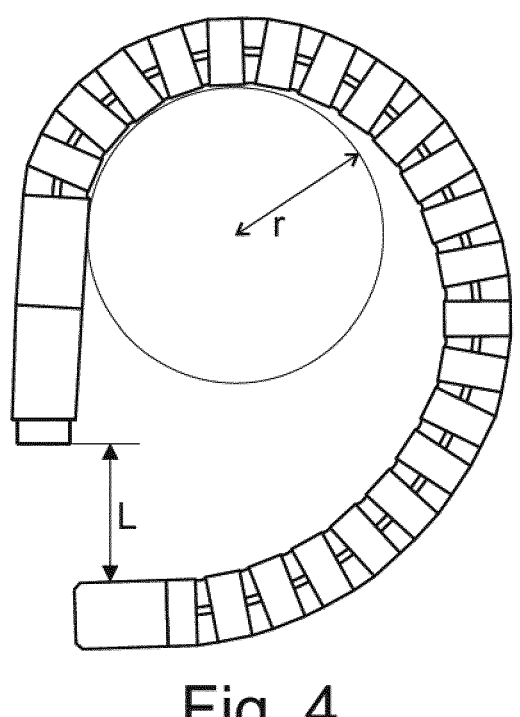
FIG. 4 is a plan view showing an ear-shaped bending profile of a bending section during bending.
Figure 5:
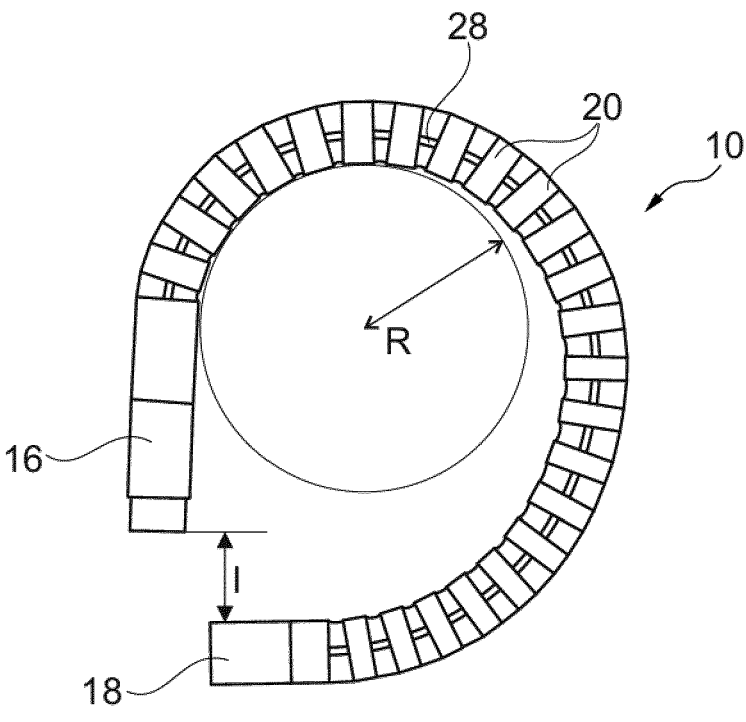
FIG. 5 is a plan view showing a rather circular bending profile of a bending section during bending.

FIG. 4 shows in this context a rather undesirable bending profile. The bending profile at a 270° bending angle is rather ear-shaped and not circular/not close to a circle. FIG. 5 on the other hand shows an optimized rather circular bending profile at a 270° bending angle. In particular, according to the bending profile of FIG. 5 a bigger bending radius R is reached at the proximal end 16 of the bending section 10 (compared to the bending radius r shown in FIG. 4), which leads to a more circular bending profile. This can in particular be seen when comparing the distance l between the proximal end 16 and the distal end 18 of the bending section 10 in FIG. 5 with the distance L between the proximal end and the distal end of the bending section in FIG. 4. It is evident that L is much bigger than l at the shown 270° bending angle. The bending angle is the angle between an orientation of the distal tip unit 12l of the distal end 18 of the bending section 10 and a longitudinally extending axis of the straight, non-bent bending section 10. Therefore, the bending angle of 270° means that the distal tip unit 12 "looks" directly onto the insertion tube 8 connected to the proximal end 16 of the bending section 10.

Figures 6, 7, 8, 9:
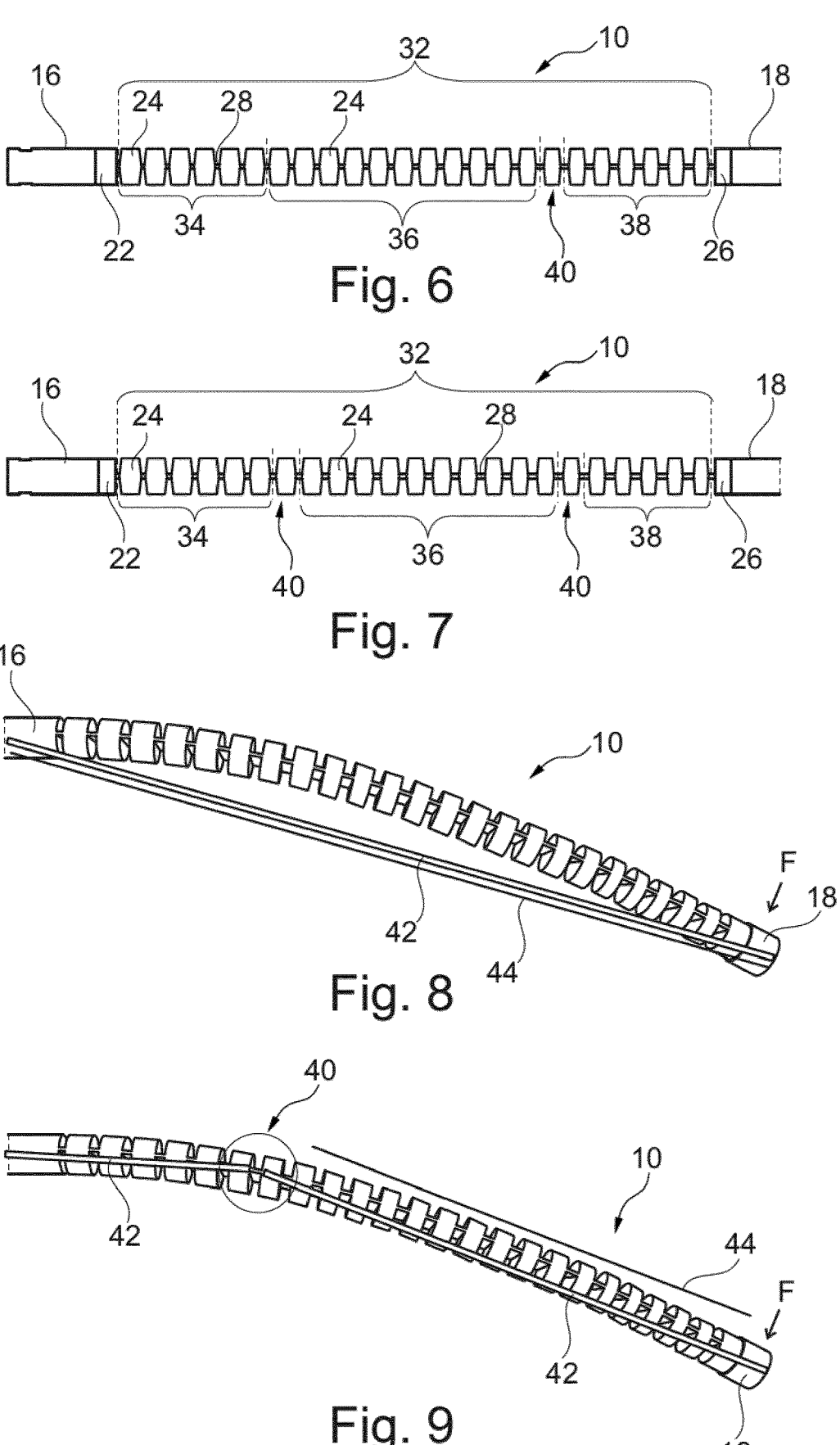
FIG. 6 is a plan view showing a bending section in accordance with a first preferred embodiment.
FIG. 7 is a plan view showing a bending section in accordance with a second preferred embodiment.
FIG. 8 is a perspective view showing a bending behavior of a bending section having no trigger point.
FIG. 9 is a perspective view showing a bending behavior of a bending section having a trigger point.

FIG. 6 shows a first preferred embodiment of a variable hinge design in accordance with the present disclosure. In particular, FIG. 6 shows a portion 32 of the bending section 10, in which the hinge length hl predominantly/overall increases in the proximal-distal-direction. Although all hinges 28 contained in the bending section 10 of FIG. 6 are part of the indicated portion 32, it is to be understood that it may also be provided that a hinge 28/some hinges 28 of the bending section 10 do not form part of the portion 32. The portion 32 thus may also be defined such that not all hinges 28 of the bending section 10 are comprised in the portion 32.

The portion 32 comprises three (sub)sections, namely a first (sub)section 34, a second (sub)section 36 and a third (sub)section 38, arranged in this order in the proximal-distal-direction, as shown in FIG. 6.

In the first (sub)section 34, the hinge length hl increases gradually from the end of the first (sub)section 34 that is closer to the proximal end 16 of the bending section 10 to the end of the first (sub)section 34 that is closer to the distal end 18 of the bending section 10. The hinge length hl between the proximal end segment 22 and the adjacent intermediate segment 24 may e.g. be 0.30 mm. In the first (sub)section 34, the hinge length preferably gradually/continuously/stepwise increases from 0.30 mm to 0.45 mm. The last hinge in the first subsection 34 may be at least 40%, preferably 50%, longer than the first hinge in the first subsection 34, with at least some of the hinges 28 between the first and last increasing in length in the proximal-distal direction.

In the second (sub)section 36, the hinges 28 have all the same hinge length hl. The second (sub)section 36 is thus preferably a section of equal hinge lengths hl. The hinge length hl is preferably 0.45 mm in the second (sub)section 36. Of course, the lengths could also change, but preferably the changes would be less than +/−30% between the first and the last hinge in the second subsection 36.

Between the second (sub)section 36 and the third (sub) section 38 a trigger point 40 is provided. At the trigger point 40, there is an abrupt increase in hinge length hl. In the present case the hinge length hl preferably increases by 0.05 mm at the trigger point 40. I.e. the hinge length hl of the distal-most hinge 28 of the second (sub)section 36 is preferably 0.45 mm and the hinge length hl of the proximal-most hinge 28 of the third (sub)section 38 is preferably 0.50 mm. One could thus say that the trigger point 40 is formed by an abrupt increase in hinge length hl over only one bending segment 20, 24 according to the embodiment shown in FIG. 6. The abrupt increase could be described as a change greater than 30% over the proximal hinge immediately preceding, proximally, the hinge with the abruptly increased length.

In the third (sub)section 38 the hinges 28 have all the same hinge length hl. The third (sub)section 38 is thus preferably also (like the second (sub)section 36) a section of equal hinge lengths hl. The hinge length hl is preferably 0.50 mm in the third (sub)section 38. Of course, the lengths could also change, but preferably the changes in length would be less than +/−30% between the first and the last hinge in the third subsection 38.

Therefore, the hinge length hl overall/predominantly increases from the proximal end 16 to the distal end 18 from 0.30 mm to 0.50 mm. The average increase in hinge length in said embodiment can be calculated as follows: a=0.20 mm/24 segments (in the portion 32 of the bending section 10)=0.0083 mm.

FIG. 7 shows a second preferred embodiment of a variable hinge design in accordance with the present disclosure. In particular, FIG. 7 shows a portion 32 of the bending section 10, in which the hinge length hl predominantly/overall increases in the proximal-distal-direction. Although all hinges 28 contained in the bending section 10 of FIG. 7 are part of the indicated portion 32, it is to be understood that it may also be provided that a hinge 28/ some hinges 28 of the bending section 10 do not form part of the portion 32. The portion 32 thus may also be defined such that not all hinges 28 of the bending section 10 are comprised in the portion 32.

The portion 32 comprises also three (sub)sections, namely a first (sub)section 34, a second (sub)section 36 and a third (sub)section 38, arranged in this order in the proximal-distal-direction, as shown in FIG. 7.

In the first (sub)section 34, the hinge length hl increases gradually from the end of the first (sub)section 34 that is closer to the proximal end 16 of the bending section 10 to the end of the first (sub)section 34 that is closer to the distal end 18 of the bending section 10. The hinge length hl between the proximal end segment 22 and the adjacent intermediate segment 24 may e.g. be 0.30 mm. In the first (sub)section 34, the hinge length hl preferably gradually/continuously/stepwise increases from 0.30 mm to 0.45 mm.

Between the first (sub)section 34 and the second (sub) section 36 a trigger point 40 is provided in the embodiment of FIG. 7. At the trigger point 40, there is an abrupt increase in hinge length hl. In the present case the hinge length hl preferably increases by 0.10 mm at the trigger point 40. I.e. the hinge length hl of the distal-most hinge 28 of the first (sub)section 34 is preferably 0.45 mm and the hinge length hl of the proximal-most hinge 28 of the second (sub)section 36 is preferably 0.55 mm.

In the second (sub)section 36, the hinges 28 have all the same hinge length hl. The second (sub)section 36 is thus preferably a section of equal hinge lengths hl. The hinge length hl is preferably 0.55 mm in the second (sub)section 36.

Between the second (sub)section 36 and the third (sub) section 38 another trigger point 40 is provided. At the trigger point 40, there is also an abrupt increase in hinge length hl. In the present case the hinge length hl preferably increases by 0.05 mm at said trigger point 40. I.e. the hinge length hl of the distal-most hinge 28 of the second (sub)section 36 is preferably 0.55 mm and the hinge length hl of the proximal-most hinge 28 of the third (sub)section 38 is preferably 0.60 mm.

One could also say that both trigger points 40 of the embodiment shown in FIG. 7 are thus formed by an abrupt increase in hinge length hl over only one bending segment 20, 24.

In the third (sub)section 38 the hinges 28 have all the same hinge length hl. The third (sub)section 38 is thus preferably also (like the second (sub)section 36) a section of equal hinge lengths hl. The hinge length hl is preferably 0.60 mm in the third (sub)section 38.

Therefore, the hinge length predominantly/overall increases from the proximal end 16 to the distal end 18 from 0.30 mm to 0.60 mm according to the embodiment shown in FIG. 7. The average increase in hinge length in said embodiment can be calculated as follows: a=0.30 mm/23 segments (in the portion 32 of the bending section 10)=0.013 mm.

Of course, as in the first embodiment, the lengths in the second and third subsections 36, 38 could also change, but preferably the changes in length would be less than +/−30% between the first and the last hinge in either subsection. The abrupt increase could be described as a change greater than 30% over the proximal hinge immediately preceding, proximally, the hinge with the abruptly increased length.

As can be seen in both FIG. 6 and FIG. 7, the length of the bending segments 20 overall/predominantly decreases in the proximal-distal-direction, i.e. as/when the hinge length hl increases.

According to the present disclosure, it has appeared that by providing an overall/predominant increasing hinge length hl in the portion 32 of the bending section 10 and by providing at least one trigger point 40 a more circular bending profile in the fully bent state (like the one shown in FIG. 5) through a more even distribution of bending forces along the length of the bending section, lower strain and stress levels in proximal hinges 28 and an earlier activation of a bending of the distal end 18 of the bending section 10 can be achieved.

Moreover, it has appeared that the second preferred embodiment comprising the two trigger points 40 achieves an 18% reduction of the strain/stress in the proximal hinges 28 compared to the first preferred embodiment. Therefore, the provision of two trigger points in accordance with the second preferred embodiment has turned out to be even more advantageous compared to the provision of only one trigger point as it is the case in the first preferred embodiment.

The effects reached in accordance with the present disclosure get even clearer when looking at FIG. 8 and FIG. 9. It has turned out that usually (uniform hinges 28/uniform hinge design or gradually increasing hinge lengths hl) the bending section 10 can be seen as one long lever 42. When a force F is applied to the distal end 18 of the bending section 10, the force F will travel on a force travel path 44 through the bending section 10 all the way to the proximal hinges 28, thus applying stress/strain to the proximal hinges 28. The force travel path 44 or lever may be also described as a moment arm. It applies that the longer the moment arm is, the bigger is the bending moment exerted in the hinge where the moment arm ends. It thus can be alternatively said that when a force F is applied to the distal end 18 of the bending section 10, the force F turns the bending section 10 into one long moment arm that exerts a high bending moment and thus high stress/strain to the proximal hinges 28.

It has turned out that by providing trigger points 40, the bending section 10 can be rather seen as a system/a series of smaller levers 42 (two in FIG. 9). In this case a certain/high amount of a force F applied at the distal end 18 of the bending section 10 travels on a force travel path 44*l* moment arm to the distal most trigger point 40 and is absorbed there. Therefore, it has shown that the provision of trigger points 40 in particular makes it possible that the bending is activated earlier in the distal end 18 of the bending section 10. This in combination with the overall/predominant increasing hinge length/the decreasing stiffness in the proximal-distal-direction makes it possible to achieve the advantages of the present disclosure (more even distribution of the bending forces, lower strain level in proximal hinges, circular bending profile).

Often there will be two hinges 28 connecting two neighboring bending segments 20. These two hinges 28 are often placed between wall parts of the bending segments 20 and may start from the periphery of the bending section 10. The two hinges 28 may be placed opposite, or substantially opposite, to each other in relation to a longitudinal extending center axis of the bending section 10. The two opposite hinges may have the same dimensions, but could also differ in width, e.g., one hinge being wider than the other.

Figure 10:
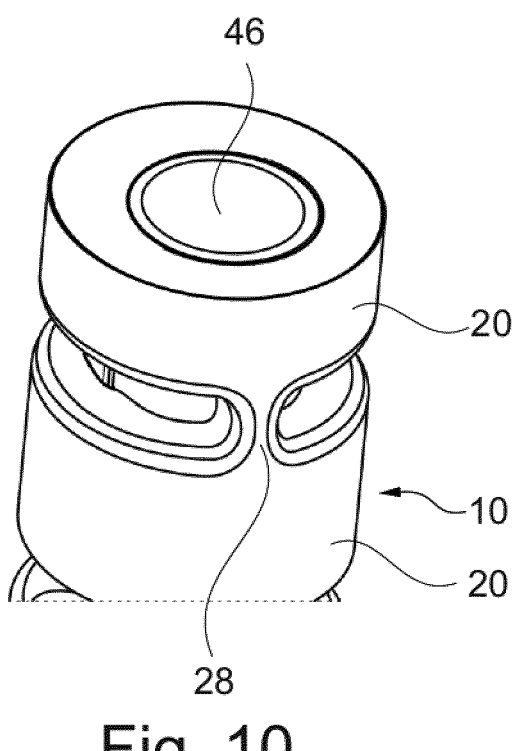
FIG. 10 is a perspective view for illustrating a manufacturing process of the bending section.
Figure 11:
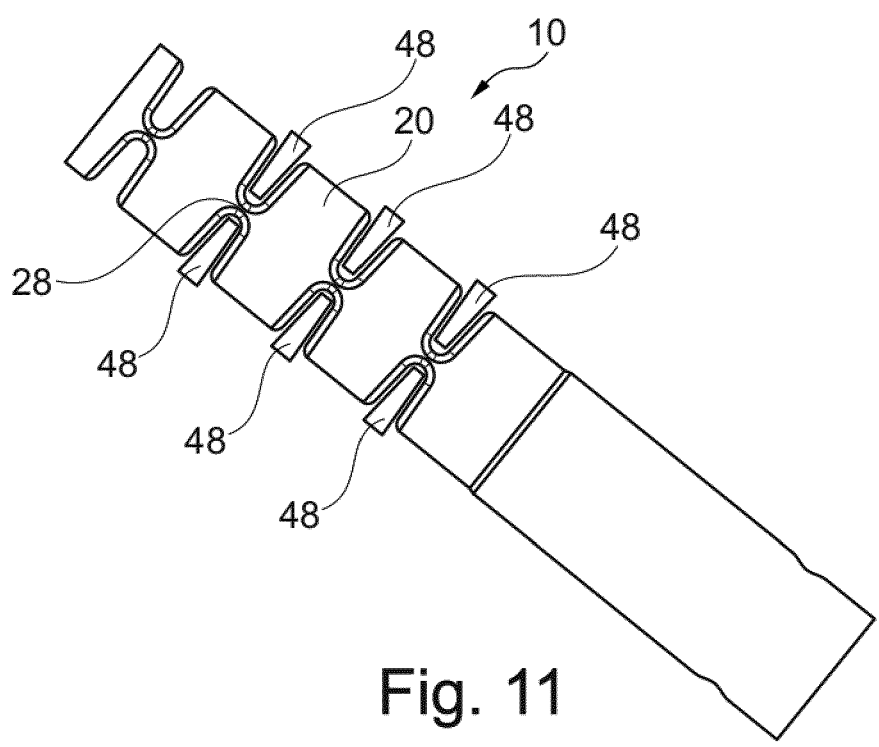
FIG. 11 is a plan view for illustrating the manufacturing process of the bending section.

FIG. 10 and FIG. 11 aim to illustrate a manufacturing process of a one-piece bending section 10 in accordance with the present disclosure. The one-piece bending section 10 is manufactured in an injection-molding process using a thermoplastic polymer material. For the injection-molding process basically a cylindrical core 46 and (steel) sliders 48 are used. As the steel sliders 48 should not be too thin, i.e. as the steel sliders 48 should provide a certain robustness, the hinge length hl typically should not be shorter than 0.3 mm. As can be easily imagined when looking at FIG. 10 and FIG. 11, the hinge length also should not be too long, in order to provide a sufficient torsional stiffness of the hinges 28. Therefore, the hinge length should not be longer than 2 mm, preferably not be longer than 1 mm, more preferably not be longer than 0.6 mm.

LIST OF REFERENCE SIGNS

2 endoscope
4 endoscope handle
6 insertion cord
8 insertion tube
10 bending section
12 distal tip unit
13 monitor
14 cable 15 operating unit
16 proximal end
18 distal end
20 bending segment
22 proximal end segment
24 intermediate segment
26 distal end segment
28 hinge
32 portion (of bending section)
34 first (sub)section
36 second (sub)section
38 third (sub)section
40 trigger point
42 lever
44 force travel path
46 cylindrical core
48 slider

The invention claimed is:

1. An endoscope comprising:
a handle; and
an insertion cord including a bending section made from
one or two pieces of polymer material, the bending
section comprising
hinges and rings formed integrally with and intercon-
nected by the hinges, the hinges comprising strips of
polymer material longitudinally separating the rings,
each of the hinges having two proximal fillets, two
distal fillets, and a length extending along a longi-
tudinal direction of the bending section, the length of
a hinge being a longitudinal distance between, and
including, the proximal fillets and the distal fillets,
a bending section portion, the lengths of at least some
of the hinges increasing in a direction from a proxi-
mal ring of said bending section portion to a distal
segment of said bending section portion,
the hinges including a first trigger hinge having an
abrupt increase in length relative to the length of a
hinge immediately proximal of the first trigger hinge,
the first trigger hinge being located between the
proximal ring of said bending section portion and the
distal ring of said bending section portion or imme-
diately adjacent, distally, the distal ring of said
bending section portion, the abrupt increase in the
length being greater than any increase between lon-
gitudinally adjacent hinges in the bending section
portion.

2. The endoscope of claim 1, further comprising a steering
control and a steering wire extending from the steering
control and through the bending section, wherein upon
actuation of the steering control the first trigger hinge bends
before hinges, of the hinges, proximal of the first trigger
hinge, the steering control comprising a lever or at least one
steering wheel.

3. The endoscope of claim 1, wherein the bending section
portion comprises
a first bending section portion; and
a second bending section portion, the second bending
section portion being distal of the first bending section
portion, wherein the first trigger hinge is located
between the first bending section portion and the sec-
ond bending section portion, wherein the lengths of the
hinges in the second bending section portion are con-
stant, wherein the hinges in the bending section portion
have constant widths, and wherein the rings in the
bending section portion have lengths, at least some of
the lengths of the rings in the bending section portion decreasing from the proximal ring of said bending
section portion to the distal ring of said bending section
portion.

4. The endoscope of claim 1, wherein:
the bending section comprises a first bending section
portion, a second bending section portion distal of the
first bending section portion, and a third bending sec-
tion portion distal of the second bending section por-
tion,
the first trigger hinge is located between the first bending
section portion and the second bending section portion,
the lengths of the hinges in the second bending section
portion are equal to the length of the first trigger hinge,
the length of the hinge immediately distal of the second
bending section portion has an abrupt increase in length
forming a second trigger hinge and being longer than
the first trigger hinge, and
the lengths of the hinges in the third bending section
portion are equal to the length of the second trigger
hinge.

5. The endoscope of claim 4, wherein the hinges in the
bending section portion have constant widths, and wherein
the rings in the bending section portion have lengths, at least
some of the lengths of the rings in the bending section
portion decreasing from the proximal ring of said bending
section portion to the distal ring of said bending section
portion.

6. The endoscope of claim 1, wherein the bending section
portion comprises
a first bending section portion,
a second bending section portion, and
a third bending section portion,
wherein the first trigger hinge is located between the first
bending section portion and the second bending section
portion or between the second bending section portion
and the third bending section portion, and wherein the
first bending section portion is different from the sec-
ond bending section portion.

7. The endoscope of claim 6, wherein the bending section
portion comprises a second trigger hinge between the second
bending section portion and the third bending section por-
tion.

8. The endoscope of claim 6, wherein the first bending
section portion is proximal of the second bending section
portion, the second bending section portion is proximal of
the third bending section portion, and the lengths of the
hinges in the second bending section portion are constant.

9. The endoscope of claim 8, wherein the lengths of the
hinges in the third bending section portion are constant and
longer than the lengths of the hinges in the second bending
section portion.

10. The endoscope of claim 6, wherein the lengths of the
hinges in the first bending section portion are devoid of the
abrupt increase.

11. The endoscope of claim 6, the hinges further com-
prising a second trigger hinge having an abrupt increase in
length, the second trigger hinge being located between the
proximal ring of said bending section portion and the distal
ring of said bending section portion, and wherein the second
trigger hinge is longer than the first trigger hinge.

12. The endoscope of claim 1, wherein the lengths of the
hinges vary from 0.3 mm to 0.6 mm, wherein the lengths of
the hinges increase by at least 0.03 mm and at most 0.15 mm
without forming the abrupt increase, and wherein the lengths
of the hinges increase by at most 0.25 mm when forming the
abrupt increase.

13. A visualization system comprising:

the endoscope of claim 1; and a monitor.

14. The endoscope of claim 1, wherein the bending section portion comprises a first bending section portion; and a second bending section portion distal of the first bending section portion, wherein pairs of the rings are connected by at least two of the hinges, the two of the hinges being on opposite sides of a longitudinally extending center axis of the bending section, wherein the first trigger hinge is located distally of the first bending section portion, and wherein the lengths of the at least some of the hinges increasing in the direction from the proximal ring of said bending section portion to the distal ring of said bending section portion are located in the first bending section portion.

15. The endoscope of claim 14, the hinges further comprising a second trigger hinge having an abrupt increase in length relative to the length of the hinge immediately proximal of the second trigger hinge, wherein the second trigger hinge is located distally of the first trigger hinge.

16. The endoscope of claim 15, wherein the second trigger hinge is longer than the first trigger hinge.

17. The endoscope of claim 15, wherein the lengths of the hinges between the first trigger hinge and the second trigger hinge are constant.

18. The endoscope of claim 17, wherein the lengths of the hinges distal of the second trigger hinge are constant.

19. The endoscope of claim 14, wherein the lengths of the hinges in the second bending section portion are constant.

20. The endoscope of claim 19, wherein the rings in the bending section portion have lengths, at least some of the lengths of the rings in the bending section portion decreasing from the proximal ring of said bending section portion to the distal ring of said bending section portion.

21. The endoscope of claim 19, wherein the hinges in the bending section portion have constant widths.

22. The endoscope of claim 14, wherein the bending section portion comprises a third bending section portion distal of the second bending section portion, wherein the lengths of the hinges in the second bending section portion are constant, and wherein the lengths of the hinges in the third bending section portion are constant.

23. The endoscope of claim 22, wherein the lengths of the hinges in the third bending section portion are constant and longer than the lengths of the hinges in the third bending section portion.

24. The endoscope of claim 23, the hinges further comprising a second trigger hinge having an abrupt increase in length relative to the length of the hinge immediately proximal of the second trigger hinge, and wherein the second trigger hinge is located between the second bending section portion and the third bending section portion.

25. The endoscope of claim 14, wherein the lengths of the hinges in the second bending section portion equal 0.45 mm and the lengths of the hinges in the third bending section portion equal 0.50 mm.

26. The endoscope of claim 14, wherein the first trigger hinge is located between the first bending section portion and the second bending section portion, wherein the rings in the first bending section portion have lengths, and wherein some of the lengths of the rings decrease in a distal direction.

27. The endoscope of claim 14, wherein the abrupt increase in length of the first trigger hinge is greater than any increase between longitudinally adjacent hinges in said first bending section portion.

28. The endoscope of claim 14, wherein the abrupt increase in length of the first trigger hinge at least 30% of the length of the hinge immediately preceding, proximally, the hinge of the first trigger hinge.

29. The endoscope of claim 14, wherein the abrupt increase is at least double of an average increase in the lengths of the hinges in the first bending section portion.

30. The endoscope of claim 14, wherein a stiffness of each of the hinges in the first bending section portion decreases in a proximal-to-distal direction, and wherein the bending section is configured to achieve an approximately circular shape when bent at a 270 degree angle.

31. The endoscope of claim 14, wherein the first trigger hinge is configured to bend before the hinges in the first bending section portion upon application of a longitudinal force at a distal end of the bending section.

*   *   *   *   *